(12) United States Patent
Liptak (10) Patent No.: US 8,440,143 B2
(45) Date of Patent: May 14, 2013

(54) AIR PURIFIER

(75) Inventor: William Joseph Liptak, West Palm Beach, FL (US)

(73) Assignee: Nordea Bank AB (publ), Stockholm (SE)

( * ) Notice: Subject to any disclaimer, the term of this patent is extended or adjusted under 35 U.S.C. 154(b) by 280 days.

(21) Appl. No.: 12/889,977

(22) Filed: Sep. 24, 2010

(65) Prior Publication Data

US 2012/0076700 A1    Mar. 29, 2012

(51) Int. Cl.
*B01J 19/08* (2006.01)

(52) U.S. Cl.
USPC .......... 422/186.3; 422/186; 422/24; 422/121; 210/748.01; 210/748.14; 96/224

(58) Field of Classification Search ............... 422/186.3, 422/186, 24, 121; 210/748.01, 748.14; 96/224
See application file for complete search history.

(56) References Cited

U.S. PATENT DOCUMENTS

| | | | |
|---|---|---|---|
| 5,516,492 A * | 5/1996 | Dong et al. | 422/186 |
| 5,564,065 A | 10/1996 | Fleck et al. | |
| 6,491,883 B2 | 12/2002 | Mori et al. | |
| 6,558,639 B1 | 5/2003 | Watanabe et al. | |
| 6,701,733 B2 | 3/2004 | Brunner | |
| 7,278,272 B2 | 10/2007 | Huston | |
| 2002/0050479 A1 | 5/2002 | Scott | |
| 2004/0130154 A1 * | 7/2004 | Stepp et al. | 285/424 |
| 2008/0152548 A1 * | 6/2008 | Clark et al. | 422/121 |
| 2010/0135864 A1 | 6/2010 | Taniguchi et al. | |
| 2010/0143205 A1 | 6/2010 | Engelhard | |
| 2010/0178199 A1 | 7/2010 | Schuman | |

FOREIGN PATENT DOCUMENTS

WO    2007086726 A1    8/2007

OTHER PUBLICATIONS

McNey, Richard: "Schuman Wants to Clear the Air", Spotlight on Queen Anne's County, Sep. 2009/Chesapeake Business Ledger, pp. 23-24.
Breathe Easy Air Purifier: "Kills Biolotical Contaminants & Stops Odors"; Dometic Marine, 2 pp., Sep. 11, 2009.
Nautic Air: "Nautic Air Wins 2008 Innovation Award at IBEX Show in Miami"; http://nauticairllc.com/html/ibex_2008.html, Oct. 21, 2008, 2 pp.
Extended European search report and written opinion for application EP/11 18 2523 dated Dec. 29, 2011.

* cited by examiner

*Primary Examiner* — Xiuyu Tai
(74) *Attorney, Agent, or Firm* — Pearne & Gordon LLP (57) ABSTRACT

An air purifier is provided, including a body comprising a wall defining an interior space, a first opening to the interior space, and a second opening to the interior space. In one example the body is a tubular body. An airflow pathway is provided through the tubular body defined between the first and second openings. A source of ultraviolet radiation is arranged to emit ultraviolet radiation into the interior space. A photocatalyst is arranged within the interior space and along the airflow pathway, and the ultraviolet radiation can be emitted onto at least a portion of the surface of the photocatalyst to activate the photocatalyst. In one example, the wall includes an aperture, and a cover is coupled to the body about the aperture and configured to enclose the source of ultraviolet radiation. In another example, the air purifier includes turbulence structure.

17 Claims, 5 Drawing Sheets

AIR PURIFIER

CROSS-REFERENCE TO RELATED APPLICATIONS

N/A.

FIELD OF THE INVENTION

The present invention relates generally to an air purifier, and more particularly, to an air purifier utilizing a source of ultraviolet radiation and a photocatalyst.

BACKGROUND OF THE INVENTION

Boats and motor vehicles, such as a RV's and long distance or over the road trucks, may be configured to provide heating, ventilating, and/or air conditioning (HVAC) needs to various locations. For example, air conditioning units have been installed on boats to provide comfortable areas on the boat during warm weather. Various methods of cooling the air on the boat have been used, including non-refrigerant cooling system, though a system using a compressed refrigerant is the most common system in widespread use today.

However, space constraints within various vehicles can be problematic. For example, it is common for air conditioning ducting to be located within the walls of boats. Conventionally, the interior space of the walls was relatively large to accommodate ducting and/or large insulation for the ducting. However, many modern boats have greatly reduced the interior space of the walls by utilizing relatively smaller, high-performance ducting and/or insulation. As such, there is a greatly reduced spacing within the walls to provide additional components, such as in-line air purifiers, etc.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, an air purifier comprises a tubular body comprising a wall defining an interior space, a first opening to the interior space, and a second opening to the interior space. The air purifier further comprises an airflow pathway through the tubular body defined between the first and second openings. A photocatalyst is arranged within the interior space and along the airflow pathway, and a source of ultraviolet radiation is arranged to emit ultraviolet radiation onto at least a portion of the surface of the photocatalyst to activate the photocatalyst.

In accordance with another aspect of the present invention, an air purifier comprises a body comprising a wall defining an interior space, a first opening to the interior space, and a second opening to the interior space. The wall comprises an aperture extending therethrough. The air purifier further comprises an airflow pathway through the body defined between the first and second openings. A photocatalyst is formed on metalized foam arranged within the interior space and comprises a surface oriented in a direction along the airflow pathway. A source of ultraviolet radiation is arranged to emit ultraviolet radiation onto at least a portion of the surface of the photocatalyst to activate the photocatalyst. A cover is coupled to the body about the aperture and is configured to enclose the source of ultraviolet radiation such that substantially all of the ultraviolet radiation emitted by the source of ultraviolet radiation is directed towards the aperture.

In accordance with another aspect of the present invention, an air purifier comprises a body comprising a wall defining an interior space, a first opening to the interior space, and a second opening to the interior space. The air purifier further comprises an airflow pathway through the body defined between the first and second openings. A photocatalyst is arranged within the interior space and comprises a surface oriented in a direction along the airflow pathway. The photocatalyst further comprises turbulence structure to generate turbulent airflow along the airflow pathway. A source of ultraviolet radiation is arranged to emit ultraviolet radiation onto at least a portion of the surface of the photocatalyst to activate the photocatalyst.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

Figure 1:
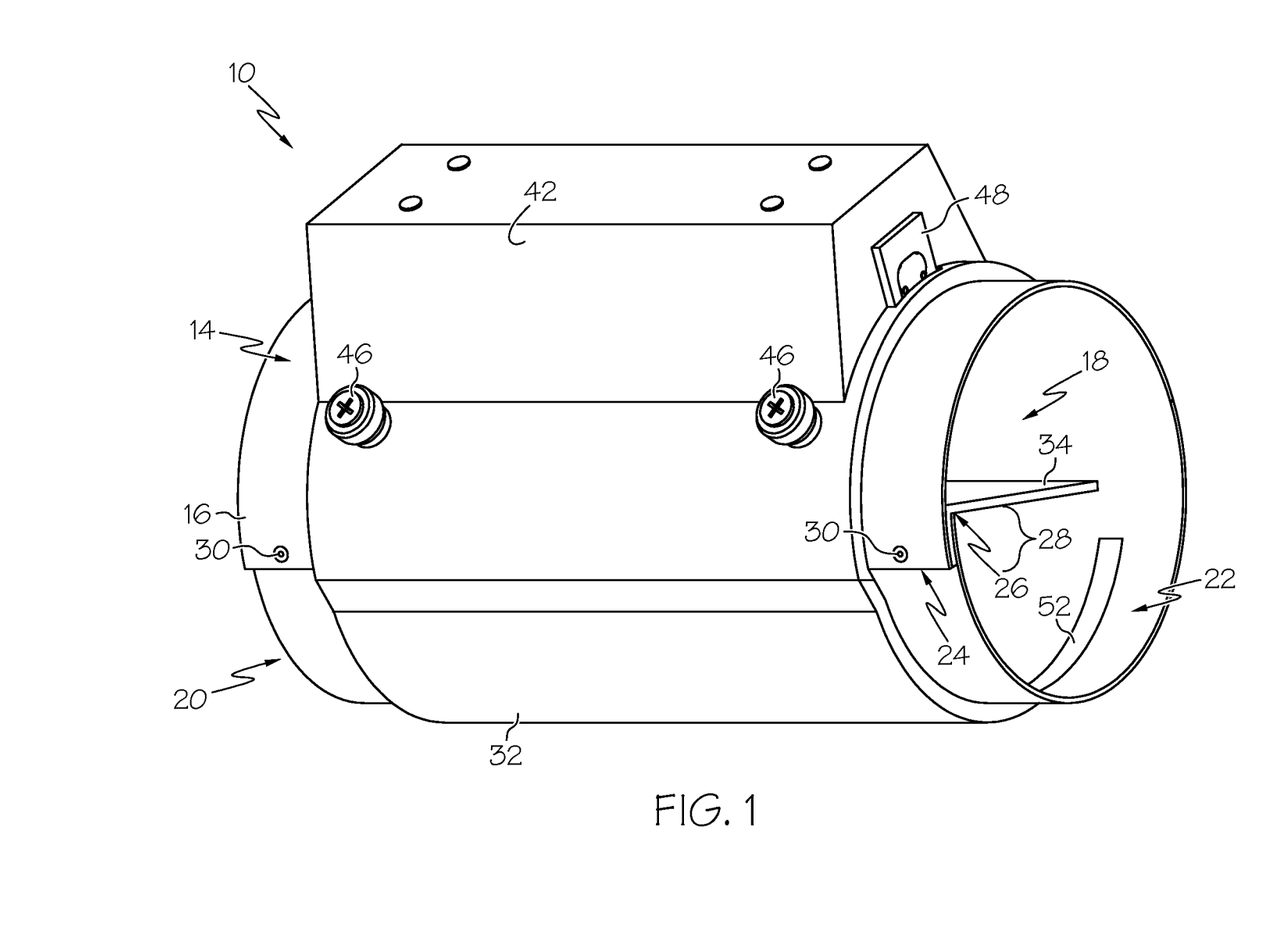
FIG. 1 illustrates a perspective view of an example air purifier.

Turning to the example of FIG. 1, an air purifier 10 is shown. The following description of the air purifier 10 is done with reference to usage in a vehicle, including boats and motor vehicles, such as a RV's and long distance or over the road trucks, etc. The interior area of a vehicle is often limited and it is often desired to reduce components within the interior area to enlarge the available space within the vehicle. Accordingly, locating various components within the interior space of the walls, floor, ceiling, or other desired spaces, can reduce the interior area required to house such components of the air conditioning system. Reducing the interior space requirements also frees additional interior space for other vehicle components and/or creature comforts that might not otherwise be installed. However, it is understood that the air purifier 10 can also be utilized in any application where it is desired to provide heating, ventilating, and air conditioning (HVAC) needs, including stationary buildings and the like.

In the example described herein, the vehicle can include an air conditioning system that can comprise a wide variety of systems configured to condition (i.e., heat, cool, and/or purify) air at various locations interior or exterior of the vehicle, such as an interior cabin, about the driver compartment, etc. In various examples (not shown), the air conditioning system might include any or all of a compressor, a condenser coil, a condenser fan, an expansion valve, an evaporator coil, an evaporator fan, a heater core, a fan, a filter, a damper/valve, a control system, various interconnecting ducting, etc. The various components of the air conditioning system can be provided together as a single assembly that can be closely contained or even spread out about the vehicle through ducting, etc. Multiple air conditioning systems can also be provided.

Figure 3:
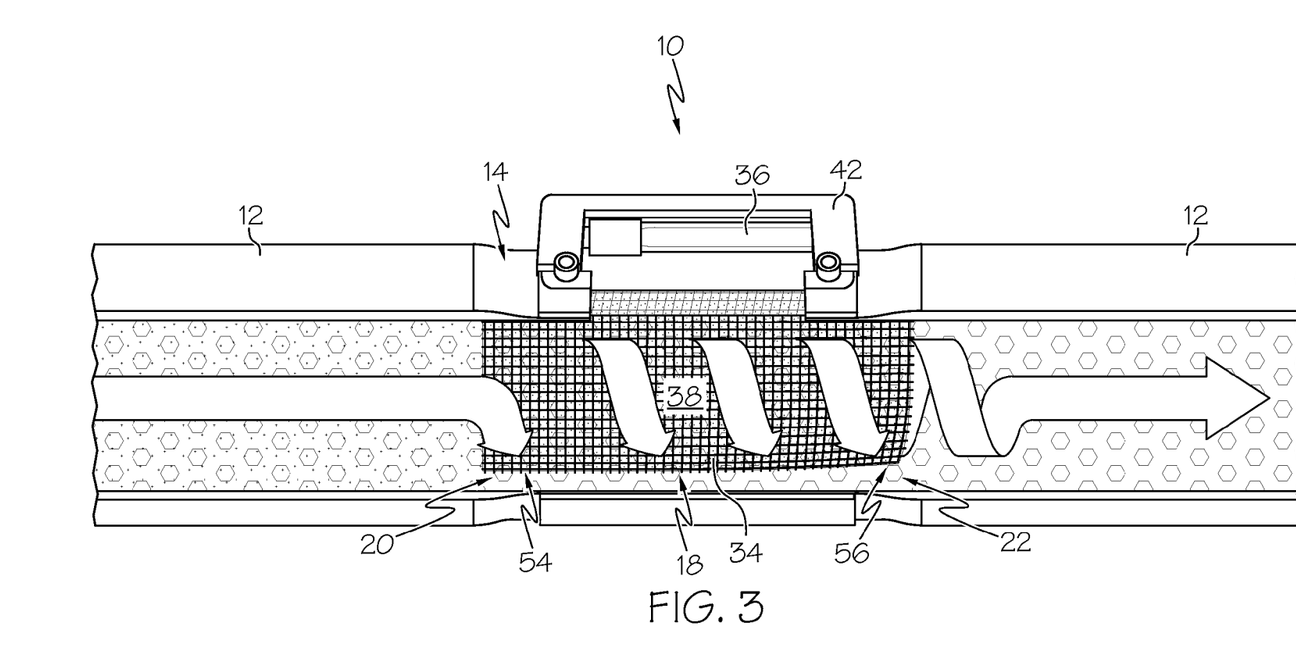
FIG. 3 illustrates a side view of the air purifier of FIG. 1 arranged in-line with example ducting.

The air purifier 10 can be arranged variously about the vehicle, and can be in fluid communication with the air conditioning system via a duct 12 (e.g., see FIG. 3). A duct 12 is a pipe, tube or channel through which a fluid, such as air, can pass. The duct 12 can be flexible, rigid and/or insulated. For example, the duct 12 illustrated in FIG. 3 can be a 6-inch duct that is insulated with ¼-inch to 1.5-inch thick insulation. To increase the interior area of a vehicle, the duct 12 may be hidden within a vehicle wall (e.g., see FIG. 5) below the floor (not shown) or in the ceiling (not shown). The duct 12 can also be disposed conspicuously within the interior area of a vehicle or disposed in another location. Conditioned air may pass through the air purifier 10 via the duct(s) 12. As such, the air purifier 10 can be located upstream or downstream of any of the various air conditioning components.

The air purifier 10 includes a body 14 including a wall 16 defining an interior space 18. The body 14 further includes a first opening 20 to the interior space 18 and a second opening 22 to the interior space 18. For example, the first opening 20 can be disposed at one end of the body 14 and can form an inlet into the interior space 18, while the second opening 22 can be disposed at another end of the body 14 to form an outlet from the interior space 18, or vice-versa. As such, an airflow pathway can extend through the body 14 defined between the first and second openings 20, 22. The wall 16 can bound substantially all of the interior space 18 such that substantially all of the fluid that enters the air purifier 10 through the first opening 20 will subsequently exit though the second opening 22.

In one example, the body 14 can be a tubular body with a generally tubular geometry, such as a cylindrical geometry with generally circular cross-section, though the body 14 can also have various other cross-sectional geometries (e.g., oval, square, rectangular, triangular, polygonal, etc.). A tubular body can be beneficial to inhibit, such as prevent, eddies or the like in the fluid that flows along the airflow pathway. For example, it can be beneficial to reduce, such as eliminating, sharp corners (e.g., square corners, angled corners, etc.) of the body 14 within the interior space 18 that can disrupt air flow. The tubular shape enables air to flow through the air purifier 10 generally unimpeded by impact with corners, perpendicular walls, and the like that can cause static pressure and/or reduce air flow. Static pressure can be detrimental to performance and to some equipment in air conditioning systems. Moreover, the connected ducting 12 usually also has a similar cross-sectional geometry (e.g., circular, etc.) such that the air can flow generally unimpeded between the inlet/outlet ducting 12 and the air purifier 10 with little change in pressure, velocity, volume, etc. Because the efficiency of air conditioning systems is related to the amount of energy used to move air throughout a vehicle while performing the air conditioning functions, reducing such disruptions to the airflow can increase the overall efficiency of the air conditioning system by reducing the amount of energy used overall.

The body 14 can be constructed variously, and can comprise a wide range of materials such as metal (e.g., aluminum, steel, etc.), plastics (e.g., thermoplastics), and/or composites. In one example, the body 14 can be a tubular body that is formed from a tubular structure, such as generally rigid pipe or the like. In another example, the wall 16 of the body 14 can include a sheet of material, such as flat sheet metal, that is formed (e.g., bent, wrapped, etc.) into the generally tubular geometry. For example, the sheet of material can include a first edge 24 and a second edge 26, and the body 14 can be formed into the tubular geometry by overlapping the first and second edges 24, 26 of the wall 16 at an overlapped seam region 28. The first and second edges 24, 26 can be removably or non-removably coupled together, such as by adhesives, welding, or fasteners 30 (e.g., rivets, bolts, screws, etc.) extending through the overlapped seam region 28 (see also FIG. 5). Alternatively, the first and second edges 24, 26 can be removably or non-removably coupled together with substantially no overlap (e.g., butt joint, fold over joint, etc.). It is also contemplated that a tubular structure can be cut lengthwise to provide the first and second edges 24, 26, if desired. It is understood that the body 14 can also be formed in various other manners, such as being cast, molded, extruded, etc.

In addition or alternatively, a wrap 32 or the like can extend at least partially, such as completely, around the body 14 to provide insulation, and/or to maintain the first and second edges 24, 26 being coupled together. The wrap 32 can also inhibit, such as prevent, condensation build-up on the body 14. For example, the wrap 32 can be ¼" foam insulation that can be held in place by gaffer's tape, though other sizes/types of insulation are contemplated.

To purify the air flowing along the airflow pathway, the air purifier 10 can further include either or both of source 36 of ultraviolet radiation, and a photocatalyst 34 capable of purifying the air by utilizing a photoreaction. The source 36 of ultraviolet radiation can be arranged to emit ultraviolet radiation into the body 14 such that the air flowing along the airflow pathway is exposed to the ultraviolet radiation. Additionally, the photocatalyst 34 can be arranged variously within the interior space 18. In one example, the photocatalyst 34 can include a surface 38 spaced apart from the wall 16 such that the surface 38 is disposed within the airflow pathway. The source 36 of ultraviolet radiation can be arranged to emit ultraviolet radiation into the interior space 18, such as onto at least a portion of the photocatalyst 34 to activate the photocatalyst 34. The source 36 of ultraviolet radiation can be arranged to emit ultraviolet radiation onto at least a portion, such as all, of the surface 38 to activate the photocatalyst 34. Thus, the source 36 of ultraviolet radiation can operate to purify the air independently of, or in cooperation with, the photocatalyst 34.

Additionally, as shown in FIG. 3, the surface 38 can be oriented along the airflow pathway, such as in a direction generally parallel to the direction of the airflow pathway (e.g., lengthwise along the air purifier 10) for contact with the air moving along the airflow pathway. This orientation can greatly reduce, such as eliminate, air resistance through the air purifier 10 so there is generally no noticeable decrease in air flow. Further, the surface 38 can extend at least partially, such as substantially completely, along the interior space between the first and second openings 20, 22 to increase the surface area for increased contact with the airborne contaminants.

Generally, photocatalytic air purification occurs when airborne contaminants physically touch a catalyst in the presence of UV light. The photocatalyst 34 purifies airborne contaminants that pass through the air purifier 10 and contact the surface of the photocatalyst 34. As air re-circulates through the air conditioning system, it makes multiple passes through the air purifier 10 for continuously improving purification levels. Photocatalytic air purification occurs when airborne contaminants physically touch the catalyst. The molecules of pollutants, odors, volatile organic compounds (VOCs), and/or biological contaminants (e.g., mold spores, bacteria, viruses, etc.) that come in contact with the photocatalyst are reconfigured into non-toxic elements. Additionally, the ultraviolet radiation reduces biological contaminants (e.g., mold spores, bacteria, viruses, etc.) that pass through the air purifier 10. As a result, significantly cleaner, healthier air exits the air purifier 10. Indeed, the air purifier 10 can output water vapor and/or carbon dioxide.

Figure 4:
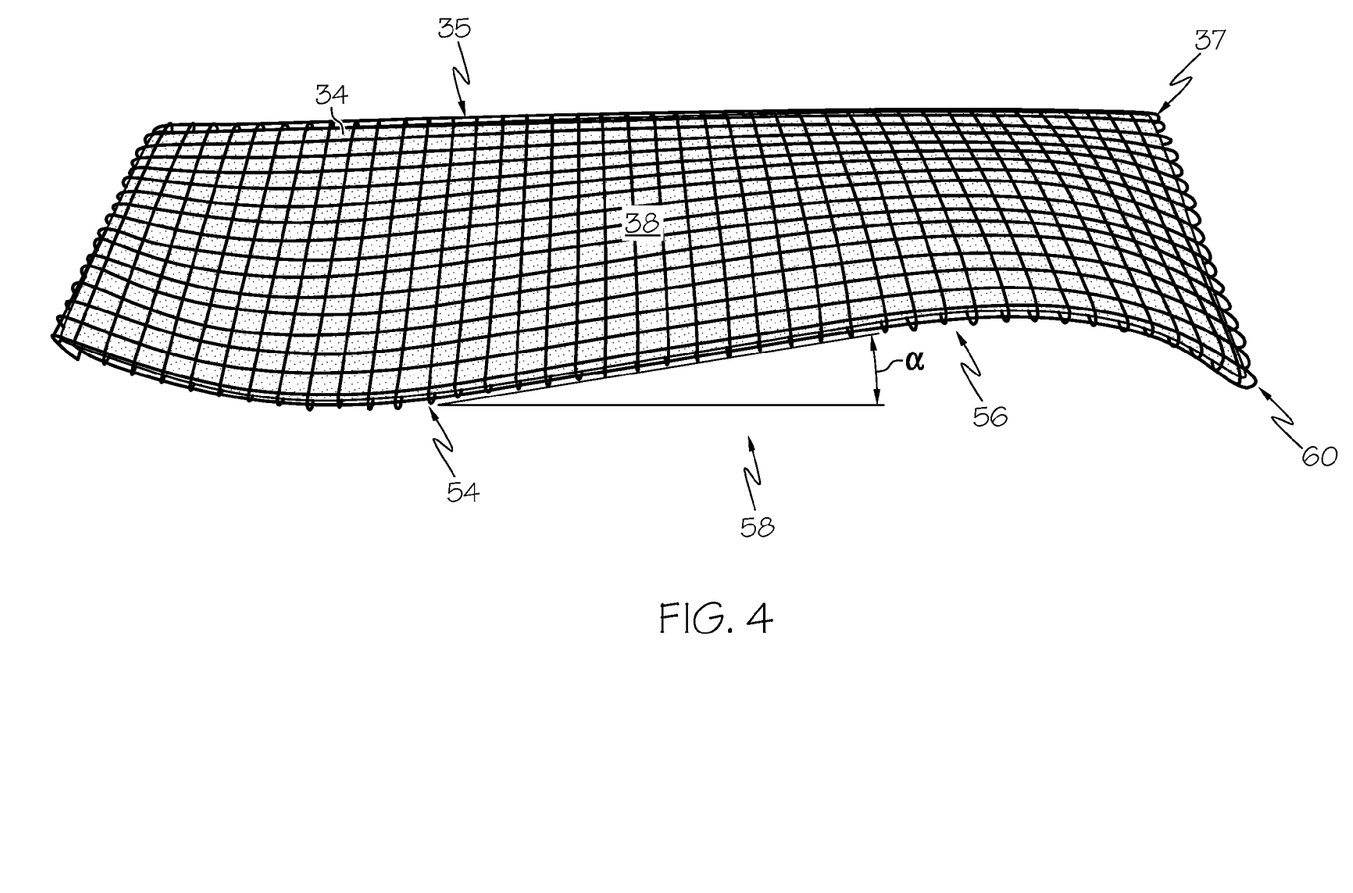
FIG. 4 illustrates an example photocatalyst.

Additionally, the photocatalyst 34 of the instant application can be formed on various base materials. In one example, the base material can be metalized foam to provide a three-dimensional photocatalytic structure. This minutely intricate construction provides a greatly increased surface area for holding the molecular catalytic coating, such as approximately 2200% more surface area as compared to a simple screen structure or flat surface, though it is understood that various base materials could be used to provide a desired amount of surface area. Thus, the photocatalyst on metalized foam can create a much greater contact surface for increased purification results. The metalized foam can be provided alone, or can be at least partially held in a supporting frame. For example, as shown in FIG. 4, the metalized foam can be enclosed in a supporting wire frame 35. For example, the wire frame 35 can be provided as a sheet-like material that is wrapped about the metalized foam. The wire frame 35 can provide mechanical support for the metalized foam within the interior space 18, and/or can provide protection from damage or the like.

The photocatalyst 34 can be removably or non-removably mounted within the interior space in various manners. For example, the photocatalyst 34 can be coupled to an inner portion of the wall 16 in various manners, including fasteners, brackets, welding, adhesives, etc. In addition or alternatively, a portion of the photocatalyst 34 can be captured (e.g., clamped, fastened, etc.) between the first and second edges 24, 26 in the overlapped seam region 28 to couple the photocatalyst 34 to the body 14 in a cantilever manner. For example, one edge 37 of the photocatalyst 34 can be bent at an angle (e.g., perpendicular or oblique), and the bent portion can be captured between the first and second edges 24, 26. The photocatalyst 34 can be coupled to the body 14 in the overlapped seam region 28 at the same time it is formed into the tubular geometry when the first and second edges 24, 26 are coupled together, or the photocatalyst 34 can be coupled in the overlapped seam region 28 at a later time. The photocatalyst 34 can even be coupled to the body 14 through the same fasteners 30 used to secure the first and second edges 24, 26 together. It is also contemplated that the wire frame 35 can facilitate mounting the photocatalyst 34 within the interior space 18. In addition or alternatively, the photocatalyst 34 can be applied to at least a portion of the inner surface of the wall 16, such as by adhesives, spray coating, etc.

The photocatalyst can include a coating of one or more various inorganic oxide particles, such as titanium dioxide. The titanium dioxide can permeate the three-dimensional structure of the metalized foam to provide a greatly increased area for reacting with the airborne contaminants. The titanium-dioxide catalyst is restructured at the molecular level to have an increased number of contact surfaces. This formation puts 70% larger molecules on the contact surface and dramatically improves reactivity with contaminants.

The ultraviolet ("UV") radiation can be provided by the source 36 in a variety of forms, including but are not limited to, sunlight, appropriately filtered incandescent bulbs, electron beam radiation, and/or lamps that emit radiation incident to an electrical discharge, such as fluorescent lamps, mercury vapor lamps, arc lamps, sodium lamps, zenon lamps, gallium lamps, or other types or even combinations thereof, including other structure or materials capable of emitting ultraviolet radiation. In one example, low-pressure or high-pressure mercury vapor discharge lamps can be used, which generate "UV" radiation incident to the mercury discharge, to cure the sealant layer. Lamps of this type generally having intensities of 20 W/cm to 400 W/cm may be used. Ultraviolet radiation sources having an emission wavelength of about 180 nm to about 450 nm are preferred. It can be beneficial to utilize a source 36 of ultraviolet radiation that has germicidal emission wavelength equal to or greater than about 254 nm to avoid generating ozone (or an insignificant amount of ozone), and/or an accumulation of undesirable substances on the photocatalyst 34.

Figure 2:
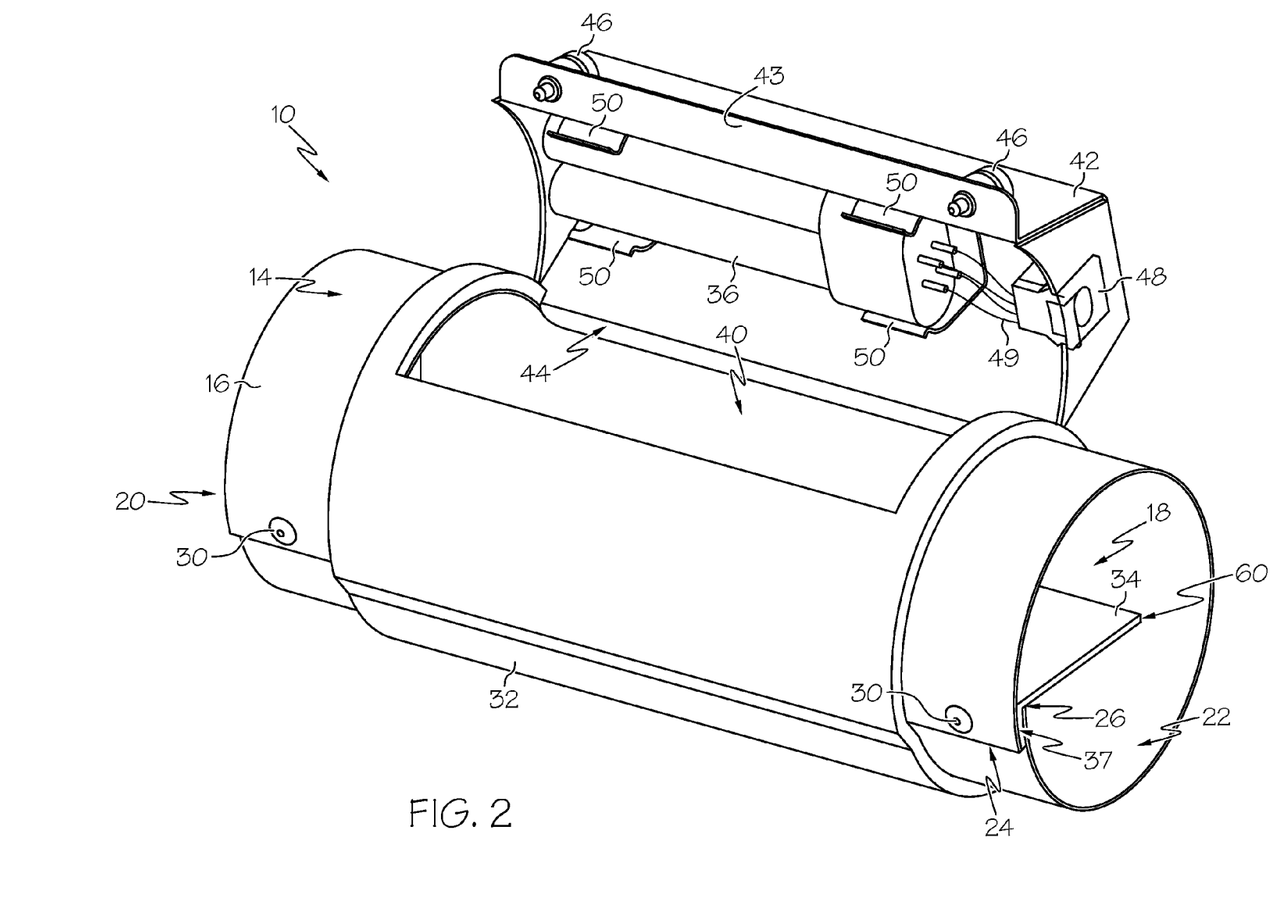
FIG. 2 is similar to FIG. 1, but shows an example cover in an alternative position.

For example, as shown in FIG. 2, the source 36 of ultraviolet radiation can be a removable or non-removable UV bulb constructed of glass, metal, quartz, or plastic. The air purifier 10 can utilize one or more sources 36 of ultraviolet radiation. For example, a pair of UV bulbs are illustrated in FIG. 2, and the dual bulbs can provide relatively greater intensity and/or service coverage to activate more of the photocatalytic material for high-performance results. The UV bulb can have various geometries, such cylindrical, u-shaped, toroidal, bulbous, or various other geometries. The UV bulb can similarly have various cross-sectional geometries, such as circular, oval, square, rectangular, triangular, polygonal, etc. In addition or alternatively, the source 36 of ultraviolet radiation can be oriented along the airflow pathway and extend at least partially along the interior space between the first and second openings 20, 22. In one example, the source 36 of ultraviolet radiation can be oriented substantially parallel to the direction of along the airflow pathway (e.g., lengthwise along the air purifier 10) to increase the area over which the ultraviolet radiation can be emitted. Such orientation can also provide the air flow with a longer exposure to the purifying UV radiation, to reduce biological contaminants like mold spores, bacteria, and viruses.

In addition or alternatively, it can be beneficial to locate the source 36 of ultraviolet radiation at least partially, such as completely, outside of the airflow pathway so as to reduce pressure loss through the air purifier 10. Thus, the wall 16 of the body 14 can include an aperture 40 extending therethrough, and the source 36 of ultraviolet radiation can be arranged to emit the ultraviolet radiation onto the surface 38 of the photocatalyst 34 via the aperture 40. As shown in FIGS. 1-3, the source 36 can be disposed substantially completely outside of the interior space 18. The aperture 40 can be configured to be at least as large as the source 36 of ultraviolet radiation, and can be much larger, to enable the source 36 to emit ultraviolet radiation over a relatively large portion, such as all, of the photocatalyst 34. For example, the aperture 40 can be oriented substantially parallel to the direction of the airflow pathway, similar to the source 36.

Additionally, the air purifier 10 can include a cover 42 coupled to the body 14 and configured to enclose the source 36 of ultraviolet radiation such that substantially all of the ultraviolet radiation emitted by the source 36 is directed towards the aperture 40. For example, the source 36 can emit ultraviolet radiation omnidirectionally. Thus, the cover 42 can be formed of a material that is opaque to, and preferably reflective of, ultraviolet radiation so that substantially all of the ultraviolet radiation emitted by the source 36 can be directed towards the photocatalyst 34. The cover 42 can comprise a wide range of materials such as plastics (e.g., thermoplastics), composites, metal (e.g., aluminum, steel, etc.). In one example, the cover 42 can be formed of sheet metal that is bent, wrapped, etc. into the desired shape. The cover 42 can also include various coatings, inserts, etc., and/or seals about the edges, that are opaque to and/or reflective of ultraviolet radiation to inhibit, such as prevent, leakage of ultraviolet radiation. In addition or alternatively, the interior of the wall 16 can also include materials, coatings, etc. that are opaque to and/or reflective of ultraviolet radiation to increase the amount of the photocatalyst 34 (e.g., upper and lower surfaces, sides, edges, etc.) exposed to the ultraviolet radiation.

The cover 42 can be removably or non-removably coupled to the body 14. In one example, the cover 42 can be completely removably from the body 14. In another example, as shown in FIG. 2, one edge 44 of the cover 42 can be pivotally coupled to the body 14 to permit access for maintenance or replacement of the source 36 of ultraviolet radiation. Another portion of the cover 42, such as another edge, can include structure to secure the cover 42 to the body 14 when it is in a closed position. The cover 42 can include an outward lip 43 or the like along said other edge to facilitate attachment of the cover to the body 14. For example, the cover 42 can include one or more fasteners 46, such as thumb screws, clips, brackets, or the like, that can be located on the outward lip 43 for removably securing the cover 42 to the body 14.

In addition or alternatively, the cover 42 can further include a socket 48 configured to removably receive the source 36 of ultraviolet radiation. The socket 48 can include electrical structure directly or indirectly coupled to the source 36 for providing electrical power thereto, such as a connector block and/or wires 49 or the like. The socket 48 can also provide mechanical support for the source 36. The socket 48 can also provide strain relief support for external electrical wires or connector block from the vehicle that provide power to the source 36. In addition or alternatively, the cover 42 can include various mechanical supports to maintain the source 36 of ultraviolet radiation within the cover 42. For example, the cover 42 can include one or more spring clips 50, brackets, fasteners, etc. to facilitate removal and replacement of the source 36.

In addition or alternatively, the air purifier 10 can further include turbulence structure configured to generate turbulent airflow along the airflow pathway. For example, the turbulent airflow can create a vortex action (i.e., spiral action) through the interior space 18 that increases, such as maximizes, surface contact of the airflow with the photocatalyst 34 to thereby increase, such as maximize, air purification. Various turbulence structure can be used. In one example, as shown in FIG. 1, the turbulence structure can include one or more fins 52 or the like disposed within the interior space 18 for imparting turbulence to the airflow. The fin(s) 52 can be provided variously within the interior space, such as coupled to an inner surface of the wall 16, etc. For example, the fin(s) 52 can impart a spin to the air flow to create a vortex action through the interior space 18. In other examples, not shown, the turbulence structure can include any or all of louvers, dampers, axial flow plates, etc. disposed variously about the air purifier 10, such as about the first and/or second openings 20, 22 and/or wall 16, etc.

In yet another example, as shown in FIGS. 3 and 4, the photocatalyst 34 can include turbulence structure. In one example, the photocatalyst 34 can include fins (not shown) or other structure to impart a spin on the air flow. In another example, the turbulence structure can include at least a first portion 54 of the photocatalyst 34 arranged at an angle α relative to a second portion 56 of the photocatalyst 34. Various portions of the photocatalyst 34, such as portion(s) of the surface 38 and/or edge(s), can be arranged at angles relative to each other. The angle(s) can be provided by sharp angles, curves, etc. Additionally, the various portions arranged at an angle can be disposed in various planes, including lengthwise along the airflow pathway, transverse to the airflow pathway, etc. The wire frame 35 can be bendable to facilitate maintaining a desired angle, shape, etc. of the photocatalyst 34.

For example, at least a portion of the photocatalyst 34 can have a generally S-shaped geometry 58 oriented along the direction of the airflow pathway (e.g., extending lengthwise along the air purifier 10). The S-shaped geometry 58 can include one or more edge(s) 60 of the photocatalyst 34, such an edge that extends outward into the airflow pathway, and/or can include some of the surface 38 of the photocatalyst 34. As shown in FIG. 4, the generally S-shaped geometry 58 can include both the edge 60 and a portion of the surface 38. The example generally S-shaped geometry 58 illustrated in FIG. 4 was created by bending the photocatalyst 34 on a 5-inch radius tube (e.g., which can provide a constant or changing angle α), though it is understood that various other bend radii (e.g., 2-inch radius tube through 10-inch radius tube, etc.) can also be used. As a result, air flowing along the photocatalyst 34 will generate turbulent airflow along the airflow pathway that can create a vortex action through the interior space 18. It is also understood that various portions of the photocatalyst 34 arranged at an angles to each other can also have other geometries, such as a U-shaped geometry, L-shaped geometry, etc. Even with such turbulence structure, it is understood that the surface 38 can still be oriented in a direction substantially parallel to the direction of the airflow pathway.

Figure 5:
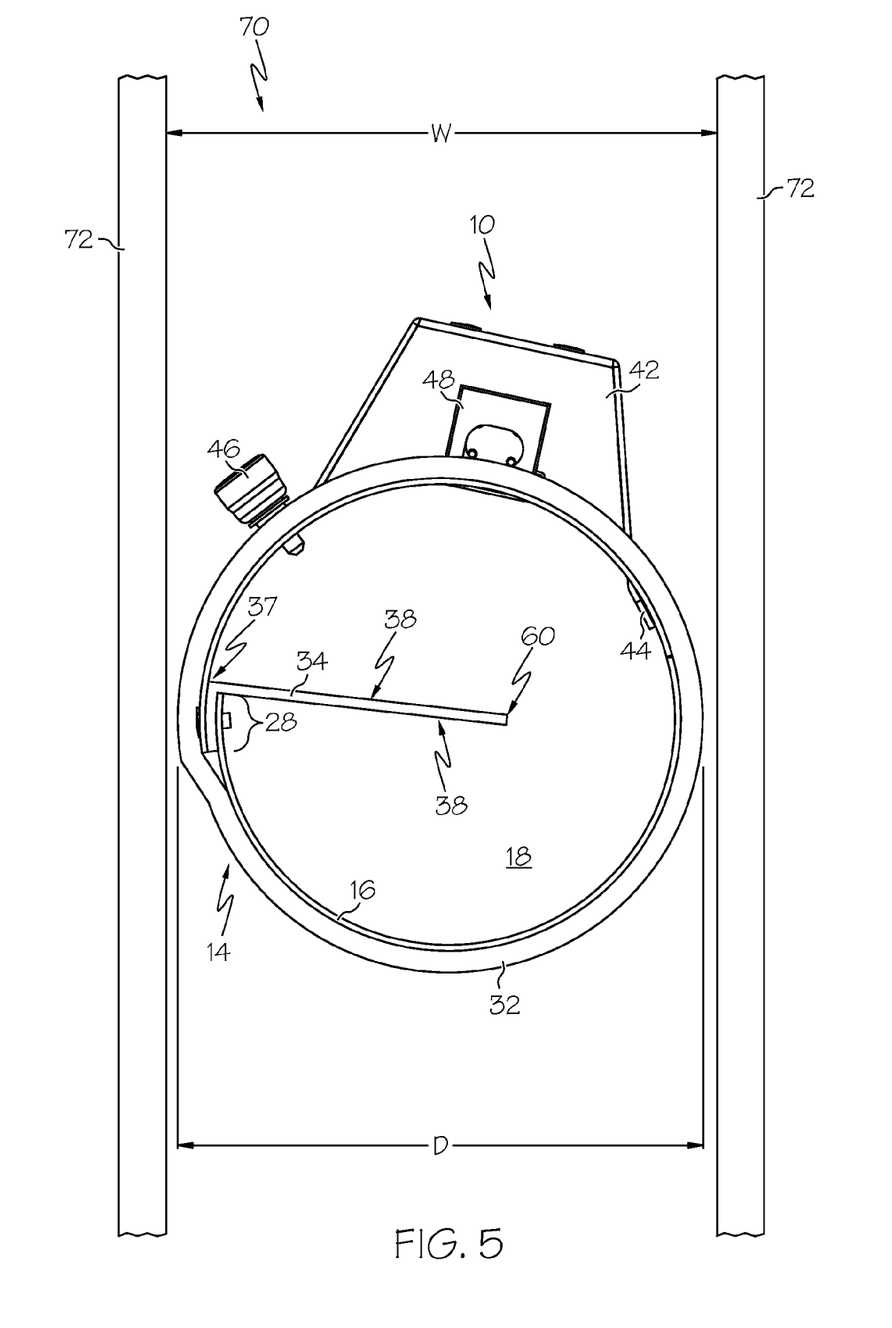
FIG. 5 illustrates a front view of the air purifier of FIG. 1 arranged within an example wall space.

Turning now to FIGS. 3 and 5, an example installation is shown of the air purifier 10 hidden within an example vehicle wall space 70 bounded by a pair of example walls 72 (or other vehicle structure). The air purifier 10 could also be hidden in the floor, ceiling, etc. As illustrated, the amount of available space within the vehicle wall space 70 is limited. The air purifier 10 is considered to be an in-duct design. That is, the air purifier 10 is directly coupled to the ducting 12 such that if the ducting 12 fits in a particular space (e.g., in a vehicle wall space 70, floor, ceiling, etc.), then the air purifier 10 should also fit. Additional benefits of in-duct (i.e., in-line) design are that the size of the body 14 generally matches the size of the ducting 12, and the overall air purifier 10 is compact for easy installation. Either or both of the first and second openings 20, 22 of the body 14 can include structure to facilitate removably or non-removably coupling the ducting 12 thereto. The ducting 12 can be held in place through various clamps, fasteners, adhesives, welding, gaffer's tape, friction fit, etc.

Thus, the limited amount of space within the vehicle wall space 70, for example limited by a width W between the walls 72, can thereby limit the amount of equipment used therein. Thus, the overall width D of the air purifier 10, including the width of the body 14 and the wrap 32 (i.e., insulation), should be substantially equal to or less than the width W. As shown in FIG. 5, is it understood that the width D of the air purifier 10 may not include the extra width provided by the cover 42 because such extra width can be accommodated by rotating or otherwise positioning the air purifier 10 within the vehicle wall space 70. For example, where the body 14 has a generally cylindrical geometry and the ducting has a corresponding generally circular cross-section, the air purifier 10 can be selectively rotatable about a longitudinal axis (e.g., about the airflow pathway, etc.) to achieve a desired installation orientation. Spacing may be provided in the vehicle wall space 70 for opening the cover 42 for maintenance of the source 36 of ultraviolet radiation. It is understood that the air purifier 10 can be removably or non-removably supported variously within the vehicle wall space 70, such as by the ducting 12, the wall(s) 72, insulation, brackets, and/or other support(s).

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. An air purifier, comprising:
a tubular body with a longitudinal axis and comprising a wall defining an interior space, a first opening to the interior space, and a second opening to the interior space;
an airflow pathway extending along the longitudinal axis through the tubular body defined between the first and second openings;
a photocatalyst arranged within the interior space and comprising a major surface extending lengthwise along a substantial portion of the airflow pathway; and
a source of ultraviolet radiation arranged to emit ultraviolet radiation onto at least a portion of the major surface of the photocatalyst to activate the photocatalyst, wherein the wall of the tubular body comprises a sheet of material comprising a first edge and a second edge, and the tubular body is formed by overlapping the first and the second edges of the wall, and
wherein a portion of the photocatalyst is captured between the overlapped first and second edges to couple the photocatalyst to the tubular body such that the major surface is supported along the airflow pathway in a cantilever manner.

2. The air purifier of claim 1, wherein the wall comprises an aperture extending therethrough, and the source of ultraviolet radiation emits the ultraviolet radiation onto the major surface of the photocatalyst via the aperture.

3. The air purifier of claim 2, further comprising a cover coupled to the tubular body and configured to enclose the source of ultraviolet radiation such that substantially all of the ultraviolet radiation emitted by the source of ultraviolet radiation is directed towards the aperture.

4. The air purifier of claim 3, wherein the cover further comprises a socket configured to removably receive the source of ultraviolet radiation.

5. The air purifier of claim 1, wherein the photocatalyst comprises a coating of titanium dioxide.

6. The air purifier of claim 1, wherein the photocatalyst is formed on metalized foam.

7. The air purifier of claim 1, wherein the photocatalyst major surface is spaced apart from the wall and oriented in a direction substantially parallel to the direction of the airflow pathway and extending substantially completely along the interior space between the first and second openings.

8. The air purifier of claim 1, wherein the source of ultraviolet radiation is oriented substantially parallel to the direction of the airflow pathway.

9. The air purifier of claim 1, further comprising turbulence structure configured to generate turbulent airflow along the airflow pathway.

10. The air purifier of claim 9, wherein the turbulence structure comprises at least a first portion of the photocatalyst being arranged at an angle relative to a second portion of the photocatalyst.

11. The air purifier of claim 10, wherein at least a portion of the photocatalyst has a generally S-shaped geometry oriented along the direction of the airflow pathway.

12. An air purifier, comprising:
a curved body comprising a wall defining an interior space, a first opening to the interior space, and a second opening to the interior space, the wall comprising an aperture extending therethrough;
an airflow pathway through the body defined between the first and second openings;
a photocatalyst formed on metalized foam arranged within the interior space and comprising a major surface oriented in a direction along the airflow pathway, an edge that extends outward into the airflow pathway, and another edge coupled to an inner portion of the wall;
a source of ultraviolet radiation arranged to emit ultraviolet radiation onto at least a portion of the major surface of the photocatalyst to activate the photocatalyst; and
a cover coupled to the body about the aperture and configured to enclose the source of ultraviolet radiation such that substantially all of the ultraviolet radiation emitted by the source of ultraviolet radiation is directed towards the aperture.

13. The air purifier of claim 12, further comprising turbulence structure configured to generate turbulent airflow along the airflow pathway.

14. The air purifier of claim 13, wherein the turbulence structure comprises at least a first portion of the photocatalyst being arranged at an angle relative to a second portion of the major surface of the photocatalyst.

15. The air purifier of claim 12, wherein the major surface of the photocatalyst is oriented substantially parallel to the direction of the airflow pathway and extends substantially completely along the interior space between the first and second openings.

16. An air purifier, comprising:
a curved body comprising a wall defining an interior space, a first opening to the interior space, and a second opening to the interior space;
an airflow pathway through the body defined between the first and second openings;
a photocatalyst arranged within the interior space and comprising a major surface oriented in a direction along the airflow pathway, an edge that extends outward into the airflow pathway, and another edge coupled to an inner portion of the wall, the photocatalyst further comprising turbulence structure to generate turbulent airflow along the airflow pathway,
wherein the turbulence structure comprises at least a first portion of the photocatalyst being arranged at an angle relative to a second portion of the major surface of the photocatalyst; and
a source of ultraviolet radiation arranged to emit ultraviolet radiation onto at least a portion of the major surface of the photocatalyst to activate the photocatalyst.

17. The air purifier of claim 16, wherein the wall comprises an aperture extending therethrough, and a cover is coupled to the body about the aperture and configured to enclose the source of ultraviolet radiation such that substantially all of the ultraviolet radiation emitted by the source of ultraviolet radiation is directed towards the aperture.

* * * * *

UNITED STATES PATENT AND TRADEMARK OFFICE
CERTIFICATE OF CORRECTION

PATENT NO. : 8,440,143 B2
APPLICATION NO. : 12/889977
DATED : May 14, 2013
INVENTOR(S) : William Joseph Liptak It is certified that error appears in the above-identified patent and that said Letters Patent is hereby corrected as shown below:

On the Title Page, item (73) in the patent details, "Assignee", please delete "Nordea Bank AB (publ), Stockholm (SE)" and insert -- Domestic Corporation, Elkart, IN (US) --

Signed and Sealed this
Sixth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,440,143 B2 | Page 1 of 1 |
| APPLICATION NO. | : 12/889977 | |
| DATED | : May 14, 2013 | |
| INVENTOR(S) | : William Joseph Liptak | |

It is certified that error appears in the above-identified patent and that said Letters Patent is hereby corrected as shown below:

On the Title Page, item (73) in the patent details, "Assignee", please delete "Nordea Bank AB (publ), Stockholm (SE)" and insert -- Dometic Corporation, Elkart, IN (US) --

This certificate supersedes the Certificate of Correction issued August 6, 2013.

Signed and Sealed this
Seventeenth Day of September, 2013

Teresa Stanek Rea
*Deputy Director of the United States Patent and Trademark Office*